(12) United States Patent
Mueller

(10) Patent No.: US 10,126,759 B2
(45) Date of Patent: Nov. 13, 2018

(54) DEVICE, SYSTEM AND METHOD FOR MONITORING, DISPLAY OF INFORMATION AND OPERATION OF MEDICAL FLUID MANAGEMENT MACHINES

(71) Applicant: Fresenius Medical Care Deutschland GmbH, Bad Homburg (DE)

(72) Inventor: Carsten Mueller, Euerbach (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 352 days.

(21) Appl. No.: 14/044,181

(22) Filed: Oct. 2, 2013

(65) Prior Publication Data

US 2014/0121845 A1     May 1, 2014

Related U.S. Application Data

(60) Provisional application No. 61/718,412, filed on Oct. 25, 2012.

(30) Foreign Application Priority Data

Oct. 25, 2012   (DE) .......................... 10 2012 020 945

(51) Int. Cl.
G05D 7/06 (2006.01)
A61M 1/14 (2006.01)
(Continued)

(52) U.S. Cl.
CPC .............. *G05D 7/0629* (2013.01); *A61M 1/14* (2013.01); *A61M 5/1413* (2013.01);
(Continued)

(58) Field of Classification Search
CPC .............. G05D 7/0629; A61M 5/1413; A61M 5/14212; A61M 1/14; A61M 5/145;
(Continued)

(56) References Cited

U.S. PATENT DOCUMENTS

| 6,676,621 | B1 |   | 1/2004 | Menninger |
| 7,918,993 | B2 | * | 4/2011 | Harraway ............... A61M 1/16 |
|   |   |   |   | 210/143 |

(Continued)

FOREIGN PATENT DOCUMENTS

| CN | 102470205 | 5/2012 |
| DE | 19849787 | 2/2000 |

(Continued)

OTHER PUBLICATIONS

Kirsch et al. "Monitoring Chronically Ill Patients Using Mobile Technologies," IBM Systems Journal, IBM Corp. vol. 46, No. 1, Jan. 1, 2007, pp. 85-93.

*Primary Examiner* — Charles Kasenge
(74) *Attorney, Agent, or Firm* — Jacobson Holman, PLLC.

(57) ABSTRACT

The invention is in the field of medical fluid management machines, in particular dialysis machines. The invention is based on the problem of expanding the input and output devices of medical fluid management machines and creating alternative possibilities for monitoring medical fluid management machines or treatments performed using such machines. In accordance with the teaching disclosed, this problem is solved by the fact that mobile computers such as tablet PCs or smartphones can be connected mechanically to the medical fluid management machines, and there is a data transmission between the medical fluid management machine and the mobile communication device or mobile computer leading to the display of information pertaining to the medical fluid management machine or a treatment performed using this device on the display unit of the mobile communication device or the mobile computer. In addition, it is proposed that sensors of the mobile computer should be used for monitoring and/or controlling the medical fluid (Continued)

management machine or a treatment performed using the same.

16 Claims, 6 Drawing Sheets

(51) Int. Cl.
    *A61M 5/14*     (2006.01)
    *A61M 5/142*     (2006.01)
    *G16H 40/63*     (2018.01)
    *G06F 19/00*     (2018.01)
    *A61M 5/145*     (2006.01)

(52) U.S. Cl.
    CPC ......... *A61M 5/14212* (2013.01); *G06F 19/00* (2013.01); *G16H 40/63* (2018.01); *A61M 5/145* (2013.01); *A61M 5/14232* (2013.01); *A61M 2205/50* (2013.01); *A61M 2205/505* (2013.01); *A61M 2205/60* (2013.01); *A61M 2205/6063* (2013.01); *F04C 2270/0421* (2013.01)

(58) Field of Classification Search
    CPC ...... A61M 2205/6063; A61M 5/14232; A61M 2205/60; A61M 2205/50; A61M 2205/505; G06F 19/3406
    See application file for complete search history.

(56) References Cited

U.S. PATENT DOCUMENTS

| | | | | |
|---|---|---|---|---|
| 8,543,420 B2* | 9/2013 | Darby | ............... | A61M 1/16 705/3 |
| 8,684,927 B2* | 4/2014 | Basaglia | ............ | G06F 19/3406 600/301 |
| 8,905,959 B2* | 12/2014 | Basaglia | ................. | A61M 1/14 604/4.01 |
| 9,117,012 B2* | 8/2015 | Basaglia | ................. | A61M 1/16 |
| 9,138,520 B2* | 9/2015 | White | ................. | A61M 1/1656 |
| 9,162,021 B2* | 10/2015 | White | ................. | A61M 1/1656 |
| 9,189,597 B2* | 11/2015 | Bluemler | ................. | A61M 1/14 |
| 2001/0027384 A1 | 10/2001 | Schulze et al. | | |
| 2001/0031944 A1* | 10/2001 | Peterson | ........... | A61M 5/14228 604/65 |
| 2002/0126036 A1* | 9/2002 | Flaherty | ............. | A61B 5/14532 341/176 |
| 2004/0158193 A1* | 8/2004 | Bui | ........................ | A61M 5/172 604/65 |
| 2004/0235446 A1* | 11/2004 | Flaherty | ............. | A61B 5/14532 455/352 |
| 2007/0112603 A1* | 5/2007 | Kauthen | ................ | G06F 19/322 705/3 |
| 2008/0024294 A1* | 1/2008 | Mazar | ...................... | H04K 3/41 340/539.12 |
| 2010/0137693 A1 | 6/2010 | Porras | | |
| 2011/0028881 A1* | 2/2011 | Basaglia | ................. | A61M 1/14 604/4.01 |
| 2011/0028882 A1* | 2/2011 | Basaglia | ................. | A61M 1/16 604/4.01 |
| 2011/0054352 A1 | 3/2011 | Ko et al. | | |
| 2012/0212434 A1* | 8/2012 | Bluemler | ................. | A61M 1/14 345/173 |
| 2012/0252543 A1* | 10/2012 | Cho | ..................... | F16M 11/041 455/575.8 |
| 2013/0018355 A1* | 1/2013 | Brand | ................. | G06F 19/3418 604/500 |
| 2013/0020237 A1* | 1/2013 | Wilt | .................... | A61M 1/1037 210/85 |
| 2013/0037485 A1* | 2/2013 | Wilt | .................... | A61M 1/1037 210/646 |
| 2013/0068915 A1* | 3/2013 | Yang | ..................... | F16M 11/041 248/551 |
| 2013/0099087 A1* | 4/2013 | Li | ........................ | F16M 11/041 248/551 |
| 2013/0133036 A1* | 5/2013 | Wang | ................. | G06F 19/3418 726/4 |

FOREIGN PATENT DOCUMENTS

| | | |
|---|---|---|
| DE | 102010019107 | 11/2011 |
| DE | 102011107795 | 1/2013 |
| WO | WO 01/28416 | 4/2001 |
| WO | WO 2007/126360 | 11/2007 |
| WO | WO 2009/122277 | 10/2009 |

* cited by examiner

DEVICE, SYSTEM AND METHOD FOR MONITORING, DISPLAY OF INFORMATION AND OPERATION OF MEDICAL FLUID MANAGEMENT MACHINES

The present invention relates to the field of medical fluid management machines, in particular a device, a system and a method for monitoring, display of information and operation of a medical fluid management machine.

STATE OF THE ART

Medical fluid management machines are understood in particular to be devices for channeling, treating and/or distributing liquids and/or gases in which fluid is transported through a fluid line between a patient and a fluid treatment component and/or a fluid source.

Fluid management machines are also understood in particular to include fluid treatment machines, such as blood treatment machines, in which fluid from a patient is supplied to a fluid treatment component through a fluid line, treated by the fluid treatment component and returned to the patient through the fluid line, which may be divided into an arterial branch and a venous branch. Examples of such blood treatment machines include hemodialysis machines in particular. One such blood treatment machine is the subject matter of DE 198 49 787 C1 by the present applicant, the contents of which are herewith completely incorporated into the disclosure content of the present patent application.

Dialysis is a method for purifying the blood of patients with acute or chronic renal insufficiency. A fundamental distinction is made here between methods using an extracorporeal blood circulation, such as hemodialysis, hemofiltration or hemodiafiltration, and peritoneal dialysis, which does not have an extracorporeal blood circulation.

In hemodialysis, blood in an extracorporeal circulation is passed through the blood chamber of a dialyzer, which is separated from a dialysis fluid chamber by a semipermeable membrane. A dialysis fluid containing the blood electrolytes in a certain concentration flows through the dialysis fluid chamber. The substance concentration of the blood electrolytes in the dialysis fluid corresponds to the concentration in the blood of a healthy person. During the treatment, the patient's blood and the dialysis fluid are passed by both sides of the semipermeable membrane, usually in countercurrent at a predetermined flow rate. The substances that must be eliminated in urine diffuse through the membrane from the blood chamber into the chamber for the dialysis fluid while electrolytes present in the blood and in the dialysis fluid at the same time diffuse from the chamber of the higher concentration into the chamber of the lower concentration. If a pressure gradient builds up on the dialysis membrane from the blood side to the dialysate side, for example, due to a pump which is withdrawing dialysate from the dialysate circulation downstream from the dialysis filter on the dialysate side, water goes from the patient's blood through the dialysis membrane and into the dialysate circulation. This ultrafiltration process leads to the desired withdrawal of water from the patient's blood.

In hemofiltration, a transmembrane pressure is applied in the dialyzer to withdraw ultrafiltrate from the patient's blood without passing dialysis fluid over the side of the membrane of the dialyzer opposite the patient's blood. In addition, a sterile and pyrogen-free substituate solution may be added to the patient's blood. This is called predilution or postdilution, depending on whether this substituate solution is added upstream or downstream from the dialyzer. Mass exchange takes place through convection in hemofiltration.

Hemodiafiltration combines the methods of hemodialysis and hemofiltration. A diffusive mass exchange takes place between the patient's blood and the dialysis fluid through the semipermeable membrane of a dialyzer, while there is also a filtering of plasma water through a pressure gradient on the membrane of the dialyzer.

The methods of hemodialysis, hemofiltration and hemodiafiltration, combined below under the heading of hemodialysis, are usually performed using automatic hemodialysis machines such as those distributed by the present patent applicant under the designation 5008.

Plasmapheresis is a blood treatment method in which the patient's blood is separated into blood plasma and its corpuscular components (cells). The separated blood plasma is purified or replaced by a substitution solution and the purified blood plasma or the substitution solution is administered back to the patient.

In peritoneal dialysis, a catheter is inserted through the patient's abdominal wall to fill the abdominal cavity with a dialysis fluid having a concentration gradient with respect to the endogenous fluids. The toxins present in the patient's body pass through the peritoneum, acting as the membrane, and enter the abdominal cavity. After a few hours, the dialysis fluid, which is now spent, in the patient's abdominal cavity is replaced. Through osmotic processes, water can be withdrawn from the patient's blood through the peritoneum into the dialysis fluid and thus withdrawn from the patient.

The peritoneal dialysis method is usually performed with the help of automatic peritoneal dialysis machines, such as those distributed by the present applicant under the designation sleep.safe.

Dialysis machines, as an example of complex medical fluid management machines, have comprehensive functions. To control these functions, medical fluid management machines such as dialysis machines are equipped with at least one control unit, which may be embodied as a CPU (central processing unit) or as a microcontroller, programmed by software programs. Such devices are often operated by touchscreen displays. Such a touchscreen display combines an input and output device into one combined surface, which provides a touch-sensitive surface with which operator input can be detected.

Possible embodiments provide spatial separation of input and output devices, for example, being embodied as a conventional display, e.g., as a CRT (cathode ray tube) monitor, LCD (liquid crystal display), plasma or OLED (organic light-emitting device) display, as an output device and as a touchpad, which is spatially separate from the former and provides a touch-sensitive surface with which operator inputs can be detected as the input device.

Regardless of the embodiment of the input/output device, the previous embodiments of these input and output devices have in common the fact that they are inseparably connected to the medical fluid management machines. The input and output device often forms a single structural unit together with the medical fluid management machine.

Such embodiments have the disadvantage that they are expensive and involve an increased assembly and maintenance effort. Thus, expensive large-format touchscreen displays are often used, involving a great additional effort in assembly of the medical fluid management machines.

Medical fluid management machines are frequently also equipped with sensors which record the measured values based on the device itself or the treatment performed using the device.

Such sensors may be optical sensors, for example, which monitor the filling levels of containers or the flow rates of fluids, for example.

Furnishing medical fluid management machines with sensors has also proven to be a cost factor and entails an increased assembly and maintenance effort.

In addition, there are older fluid management machines in particular which are still in use but do not have a display or perhaps have only a few sensors for monitoring the fluid management machines or a treatment performed using such a machine.

DESCRIPTION

The object of the present invention is therefore to provide an improved display and operating device for medical fluid management machines. In particular a system of a medical fluid management machine and an external display and operating device and a method for use of an external display and operating device with a medical fluid management machine should also be created.

These problems are solved according to the present invention by a mobile computer according to claim 1, a medical fluid management machine according to claim 2, a system according to claim 8 and a method according to claim 9 and a method according to claim 10.

Advantageous embodiments are the subject matter of the dependent claims.

Accordingly, a mobile computer is provided for use with a medical fluid management machine, having a control unit, an input and/or output device and an interface, which is configured for data exchange with a medical fluid management machine, and having a mechanical connecting device, which is designed for connection to a suitably designed counterpart on the medical fluid management machines, and the control unit of the mobile computer is equipped to display information pertaining to the medical fluid management machine and/or a treatment performed using the medical fluid management machine on the display unit and/or operator entries entered by means of the input device and/or control signals to be forwarded over the interface to the medical fluid management machine.

In addition, a medical fluid management machine is equipped with a control unit and an interface, which is designed for data exchange with a mobile computer, and with a mechanical connecting device, which is designed for connection to a suitably designed counterpart on the mobile computer, such that the control unit is equipped to send information pertaining to the medical fluid management machine and/or a treatment performed using the medical fluid management machines to the mobile computer over the interface and/or to receive operator inputs entered on the mobile computer and/or to receive control signals from the mobile computer.

In addition, a system comprising a medical fluid management machine and a mobile computer having the properties defined above is also provided.

In addition, a method is also provided for display of information pertaining to a medical fluid management machine or a treatment performed using the medical fluid management machine for display of information pertaining to the operation of a medical fluid management machine comprising the following steps: mechanical connection of a mobile computer to the medical fluid management machine, establishing a data link between a medical fluid management machine and a mobile communication device or mobile computer, display of information pertaining to a medical fluid management machine or a treatment performed using the medical fluid management machine by means of an output device of the mobile computer or operation of the medical fluid management machine by means of an input device of the mobile computer.

Furthermore, another method is provided for monitoring and/or controlling a medical fluid management machine or a treatment performed using the medical fluid management machine, comprising the steps:

Connecting a mobile computer to the medical fluid management machine in such a way that a sensor of the mobile computer can receive/record sensor values pertaining to the medical fluid management machine or a treatment performed using the medical fluid management machine; recording the sensor values; data processing of the sensor values and, depending on the results; monitoring and/or controlling the medical fluid management machine or a treatment performed using the medical fluid management machine.

The disclosed teaching is to be explained below on the basis of a dialysis machine as a medical fluid management machine. It will be clear to those skilled in the art that the invention can readily be transferred to other medical fluid management machines. Examples include infusion devices for medical fluids, cardiovascular support machines with an extracorporeal blood circulation, liver support machines with an extracorporeal blood circulation or the like. The embodiments described below on the example of a dialysis machine as an example of a medical fluid management machine may essentially be transferred to any other medical fluid management machine.

A dialysis machine is often furnished with an expensive, relatively large display, often embodied as a touchscreen display. To save on this cost factor, it is proposed that only simple display devices for elementary important values should be installed instead of an expensive display. Such display devices may include, for example, seven-segment LED displays or LED control chains.

Older dialysis machines are often not equipped with a display. It is conceivable that such machines might be retrofitted with an inventive connecting device and a data interface to allow the use of an external mobile communication device or a mobile computer with an output device embodied as a display.

The advantage of such retrofitting is the use of inexpensive equipment, such as mobile communication devices or mobile computers, which are equipped with a display anyway without requiring any major renovation work on the dialysis machine.

Mobile communication devices are understood in particular to include mobile telephones or so-called smartphones. Smartphones are usually characterized by a comparatively large touchscreen display. In addition, smartphones usually have various computer capabilities because they are equipped with high-performance microprocessors and versatile operating systems. Smartphones may thus be programmed in any way using application programs or so-called apps. Smartphones almost always have one or more sensors.

Smartphones are often equipped with at least one camera device for recording photographs and videos. Smartphones having two cameras on opposite sides of the smartphone are also known.

Furthermore, smartphones always have a microphone, which may be used as an acoustic sensor. In addition, smartphones may be equipped with a plurality of other sensors. Examples include inclination sensors, vibration sensors or temperature sensors. Furthermore, a touchscreen display functions as a touch-sensitive sensor. Fingerprint sensors may also be components of smartphones.

In addition, mobile computers in the sense of the present disclosure are also understood to include laptops, notebooks or tablet PCs, for example. The equipment for mobile computers and smartphones may be very similar. All the equipment features of smartphones may also be present on mobile computers. The essential difference between these two device categories is the size of the device, in particular the size of the display.

Regardless of which device is used, the device that is used has a display and an interface for data exchange with the dialysis machine.

Furthermore, the mobile communication device or the mobile computer has a connecting device by means of which a mechanical connection can be established in interaction with a suitably designed connecting device on the dialysis machine. The mechanical connection between the mobile communication device or mobile computer and the dialysis machine can advantageously be released at any time in the sense of decoupling.

Such connecting devices may include: plug connectors, hooks, eyes, clamps, magnetic connections, Velcro-type closures or other devices which are suitable for establishing a mechanical connection between the dialysis machine and a mobile communication device or the mobile computer, referred to below by the umbrella term "mobile computer."

In accordance with the teaching of the present invention, the mobile computer includes at least one display, an input and/or output device, embodied as a touchscreen, for example, an interface designed for data exchange with another device, a control unit, for example, a CPU (central processing unit) and/or a microcontroller as well as a connecting device designed to make it possible to establish a mechanical connection to a medical fluid management machine.

In addition, in accordance with the teaching of the present invention, the mobile computer may have at least one sensor.

Such connecting devices in which no structural change in the external device is necessary are advantageous. In this embodiment, the connecting device on the mobile computer is the housing of the mobile computer itself, which engages in a suitably equipped connecting device of the dialysis machine. Such connecting devices of the dialysis machine may be, for example, recesses such as bays into which the mobile computer is inserted or introduced. A clamp is another example of this device.

Such a connecting device may advantageously be designed so that an electrically conducting connection can be established between the dialysis machine and the mobile computer. Clamping mechanisms embodied in this way may have, for example, plugs or sockets on a clamping jaw, which engage in a suitably shaped counterpart on the mobile computer, establish an electrical connection to same. Recesses in the dialysis machine may have electrical interfaces which establish an electrical connection when the mobile computer together with the corresponding interfaces is accommodated on the mobile computer. However, the electrical connection between the dialysis machine and the mobile computer may also be established by an electrical cable.

However, the connecting device of the mobile computer may also include a connecting device produced specifically for the mobile computer, such that the connecting device can be installed in the mobile computer. Such connecting devices include, for example, plug connectors or screw connections, which can optionally be rotatably or pivotably supported or extracted, allowing the mobile computer to be connected to the dialysis machine.

With an electrical connection between the dialysis machine and a mobile computer, a transfer of energy in the form of electricity from the dialysis machine to the mobile computer may advantageously take place. The dialysis machine may thus supply the power for the mobile computer and/or may charge the battery that is often present in a mobile computer.

However, according to the teaching of the present disclosure, data exchange between the dialysis machine and the mobile computer may also take place wirelessly. Conventional wireless data transmission pathways include a wireless transmission such as WLAN or Bluetooth, or even infrared data transmission.

In wireless transmission, a reliable correlation between the mobile computer and the dialysis machine is essential. Therefore, in the teaching according to the present disclosure, a device is provided to show on a display that a mobile computer is in the connecting device.

Such a device may include a switch or a keypad, which is operated in connecting the mobile computer. It is thus possible to ascertain whether a mobile computer is connected by having the dialysis machine make an inquiry about the switch status.

In addition, the teaching of the present disclosure provides that an authenticity check is to be performed between the mobile computer and the dialysis machine, so that data exchange takes place between the dialysis machine and the mobile computer using the devices provided for this purpose and does not take place with other unauthorized devices in the vicinity.

Such authentication with subsequent connection and initialization of wireless data transmission between the two devices may take place by means of a near field communication technology such as NFC.

In all possible exemplary embodiments, transmission protocols which are secure with respect to confidentiality, authenticity and integrity, for example, the data transmission protocols IPSec (Internet Protocol Security) or VPN (Virtual Private Network) or OpenVPN, are preferred for data transmission.

Furthermore, a data transmission protocol with secure identification of the data exchanging devices such as Bluetooth or IrDA (Infrared Data Association) may also be used for authentication of the dialysis machine and the mobile computer.

In one embodiment, the invention provides that the dialysis machine transmits information to the mobile computer, resulting in a display of data pertaining to the dialysis machine and/or a treatment performed using the dialysis machine, on the display of the mobile computer. In one embodiment, image content transmitted in this way corresponds to that of a dialysis machine that is otherwise identical, except for being equipped with an integrated display. The display functionality can be rerouted to the mobile computer in this way.

However, it is also possible to provide that the transmitted image content depends on the display properties of the mobile computer. Thus, for the sake of an overview, the screen contents on mobile computers with comparatively smaller displays such as smartphones may be reduced in comparison with mobile computers having large displays, for example, tablet PCs.

The information about the display size and resolution of a mobile computer can be transmitted in the initial connection of the mobile computer to the dialysis machine.

In an alternative embodiment, a suitably programmed mobile computer automatically adapts the display of the received video information to its display properties.

In one alternative embodiment, the input device of the mobile computer, which is embodied as a touchscreen, for example, may be used for operator input on the dialysis machine. The operator entries made on the input device of the mobile computer are further entered into the dialysis machine by means of the interface.

According to another alternative embodiment, the operating devices on the dialysis machine are to be blocked for operator input as soon as the mobile computer is connected for operation of the dialysis machine in order to prevent double entries.

To facilitate cleaning of the dialysis machine, it is possible to provide that the connecting device is retractable into the dialysis machine in such a way that preferably an uninterrupted planar housing surface is formed on the dialysis machine in the retracted state.

Another aspect relates to the use of sensors of mobile computers for the purpose of monitoring the dialysis machine. Smartphones and tablet PCs, for example, are often equipped with at least one camera device for recording photographs and videos. Embodiments having two cameras on opposite sides of the device are also known.

In addition, smartphones and tablet PCs often have a microphone, which may be used as an acoustic sensor. Furthermore, smartphones and tablet PCs may be equipped with a number of other sensors. Examples of these include inclination sensors, vibration sensors or temperature sensors. Furthermore, a touchscreen display functions as a touch-sensitive sensor. Fingerprint sensors may also be components of smartphones and tablet PCs.

According to one exemplary embodiment of the invention, the mobile computer can be mechanically and electrically connected to the dialysis machine in such a way that a camera of the mobile computer is directed at the dialysis machine or at parts of the dialysis machine.

The mobile computer can monitor and/or control the dialysis machine by appropriate programming. For example, it is possible to monitor the pump rate of hose reel pumps, such that the movement of the rotor of the hose reel pump is detected and evaluated by means of video analysis in the mobile computer. The mobile computer is programmed accordingly for the implementation of the video analysis.

In addition, filling levels in drip chambers, for example, can be detected similarly. It is also possible to monitor other medical fluids such as suspended bags with infusion solutions, for example. Thus the mobile computer can output a warning message, for example, when an infusion solution that is kept on supply threatens to run empty.

Furthermore, it is also possible to detect disturbances during operation by analysis of the camera signal. For example, a leak in the extracorporeal blood circulation can be detected because escaping blood can be detected by camera analysis. In such a case, an alarm message may be output by the mobile computer and/or control signals may be sent to the dialysis machine, resulting in the dialysis treatment being interrupted and the dialysis machine being put in a secure state, for example, by interrupting the delivery of blood through the blood pump and clamping off the arterial and venous accesses on the patient by means of appropriate hose clamps. Similarly, the mobile computer may also intervene in the control of the dialysis machine, depending on other sensor values.

Furthermore, the accessory parts that are used can be recognized by camera analysis and/or video analysis in the mobile computer. For example, the dialysis filter or inserted tube sets can be recognized on the basis of their optical properties.

For example, the mobile computer can recognize in this way whether a dialysis filter which fits the dialysis machine or has been approved for use by the manufacturer of the dialysis machine or other accessory parts are being used and can output a warning, depending on the result of this check, if an accessory part that does not fit or is not approved is being used.

In this case, the mobile computer can document such a procedure, for example, in a memory inside the device or by data transmission to an additional device. This data transmission may be done in the form of email, SMS or a pager message to a higher instance, for example, the ward physician. Another interface on the mobile computer, for example, a mobile wireless device, may be used for this purpose.

According to one embodiment, a camera on the mobile computer is directed at the patient. On the one hand, this serves to monitor the patient when the image of the camera is transmitted to additional devices for medical personnel, for example, and on the other hand, certain gestures by the patient, leading to actions associated with the respective gestures, can be recognized by video analysis in the external device. Thus a certain gesture by the patient, for example, pointing down with his thumb, may signal that the patient wants to reduce the volume of audio messages on the dialysis machine, which is then initiated by data transmission from the mobile computer to the dialysis machine.

According to another embodiment, the type of pending treatment can be revealed to the mobile computer. This may take place through the dialysis machine itself in that it prompts a corresponding data transmission to the mobile computer. However, this information can also be disclosed to the mobile computer by input on the mobile computer itself or by other data transmission pathways. It is essential that both the dialysis machine and the pending treatment are known to the mobile computer.

With this information, through suitable programming which accesses stored data for the type of upgrade of the dialysis machine for a certain treatment, the upgrading operation can be monitored and initiated.

This monitoring can monitor both the structure and the equipment process itself. For example, it is necessary in dialysis treatments to completely deaerate the dialysis filter and the extracorporeal blood circulation. The dialysis filter must be rotated by 180 degrees, for example, in deaeration, often at a certain point in time. This process can also be monitored by camera analysis.

The mobile computer may advantageously provide the user with optical and/or acoustic instructions on how the upgrade is to take place in the specific case. This may take place by means of the display on the mobile computer. Acoustic instructions may be output by means of the loudspeaker on the mobile computer, e.g., using a voice synthesizer.

Deactivation of the machine may also be monitored in a similar way. For example, certain steps are necessary in a dialysis treatment to separate a patient from the dialysis machine after the treatment has been completed. This process can also be monitored and/or instructions imparted by means of the output devices on the mobile computer.

Other sensors on the mobile computer may also be used for monitoring. In one embodiment, the mobile computer is equipped with a temperature sensor, for example, an infrared camera, which may be used in the manner already described to monitor the dialysis machine and a treatment performed using it. In the case of an infrared camera, it is also conceivable that the patient is also monitored alternatively or additionally and that the patient's body temperature, for example, is measured. High or low body temperatures in a patient may thus be detected in a non-contact operation, and corresponding instructions or warnings may be output by means of the output devices on the mobile computer.

Acoustic monitoring of the dialysis machine, the treatment performed using it or the patient may also take place by analyzing a microphone signal of the mobile computer accordingly.

Thus a specific dialysis machine with a specific upgrade will also generate a specific sound effect during a specific treatment, and this sound effect can be detected by the microphone on the mobile computer. A corresponding analysis of the microphone signal, which is done by appropriate programming of the mobile computer, can detect deviations from the expected noise signal and in this case can deliver a message by means of the output devices on the mobile computer. For better analysis, it is possible to provide that outside noises such as those which often occur within a treatment are filtered out by data processing of the microphone signal.

Another aspect of the acoustic monitoring relates to the patient himself, whose acoustic expressions can be detected by the microphone on the mobile computer. For example, abnormal sounds (moaning, wheezing) as well as statements of intent by the patient can be detected, and additional steps such as alarm messages, which are also transmissible by data transmission to other devices may also be output.

All other sensors with which the mobile computer is equipped may also be used for monitoring the dialysis machine, the dialysis treatment or the patient.

For example, a fingerprint scanner provided on the mobile computer may be used to identify the patient unambiguously. If the treatment data and the patient are known to the mobile computer, the upgrade of the dialysis machine may then be monitored, based on the known treatment data, with the help of a camera that is provided.

Regardless of which sensors the mobile computer is equipped with, they may be used to monitor the patient and/or to monitor and/or control the dialysis machine and/or the dialysis treatment.

In accordance with the teaching of the present invention, it is provided in this regard that the mobile computer can be connected to the medical fluid management machine in such a way that the corresponding sensor can detect a signal based on the medical fluid management machine and/or on a treatment performed using the medical fluid management machine. Accordingly, the control unit of the mobile computer is equipped to relay control signals to the medical fluid management machine and/or to output alarm messages, depending on the signal detected.

Another advantage in agreement with the teaching of the present invention relates to the possibility that the mobile computer stores treatment data for several treatments and makes the data available to the operator. A treatment history is formed in this way, containing valuable information for the treating physician, on the basis of which he can manage the future treatment. Frequently only limited storage options are available for storing treatment data in a conventional dialysis machine. This disadvantage can be overcome by using a mobile computer. The internal memory in a mobile computer is often more extensive than that in a dialysis machine. The memory capacity of a mobile computer can also be expanded by accessing additional external devices, for example, a network, such as a cloud service.

In addition, the mobile computer may also be used to perform calculations for which the dialysis machine is not equipped. For example, this may be the case if the dialysis machine does not have the appropriate programming, or the hardware serving the dialysis machine is not capable of performing the corresponding calculation because it is outdated, for example, or the sensor data, which would be necessary for a calculation and is recorded by the mobile computer, for example, is not available. For such calculations, the mobile computer is programmed by means of specific computer programs.

In general, the mobile computer and the medical fluid management machine have specific programs, which control the operation of the medical fluid management machine or the display of the data pertaining to the medical fluid management machine or a treatment performed using it and/or the use of sensors for monitoring and control of the medical fluid management machine or a treatment performed using it accordingly and perform the methods described in accordance with the teaching of the present invention.

These specific programs are computer programs that can be loaded directly into an internal memory in the mobile computer and/or the medical fluid management machine and include software code sections which execute the methods described when the programs are running on the mobile computer or the medical fluid management machine. The computer programs may be stored on data media as computer program products comprising computer-readable program means. These data media may be used in a computer and also include, in addition to physical memories such as diskettes, CD-ROMs, memory cards, USB sticks or DVDs, storage within networks such as the Internet to which the user can have access.

In addition, in accordance with the teaching of the present invention, all the devices and methods present in the mobile computer may advantageously be used to supplement and/or expand the functionality of a medical fluid management machine, in particular a dialysis machine.

Examples of this include the following:

The mobile computer may be used for network access and/or for connection to the Internet, since the corresponding data links, which can be established in the mobile computer, are forwarded over a data interface to the dialysis machine. Such a data link by means of the mobile computer is also known as tethering.

A treatment comparison for various patients can also be performed over such an enabled Internet connection. To do so, the current treatment parameters are compared and evaluated with the current treatments of a patient community, preferably anonymously. The evaluation principles may include, for example: height, weight, race/ethnicity and blood values as well as type of machine and the treatment or therapy performed using that machine.

Mobile computers are often also equipped with a device for determining the location of the machine, for example, by a GPS (global positioning system) sensor or by analysis of local network connections. This information may also advantageously be utilized to influence the dialysis machine or a treatment performed using it in accordance with the teaching of the present invention.

For example, based on information about the location of the dialysis machine, information about the usual water quality at this location can also be derived, which may in turn have an effect on the preparation of solutions prepared with the dialysis machine.

In addition, on the basis of information about the location of the dialysis machine, it is also possible to recognize whether certain treatment options are allowed at this location and/or whether they are paid for the by the local health insurance companies. Alternatively or additionally, a treatment option can also be enabled if payment of this option has been confirmed. This may also be handled by a suitable application in the mobile computer, for example, by entering credit card data. Payment methods which make use of an Internet connection may also be used. These are known by the term e-commerce (electronic commerce).

What many embodiments have in common is that the mobile computer communicates with at least one other device besides the medical fluid management machine. This other device may be, for example, another computer embodied as a server, for example, a pager or a mobile wireless device.

The present disclosure includes the use of mobile computers as input or output devices as well as control and/or monitoring devices and the use of methods and equipment of mobile computers, for example, sensor devices, medical fluid management machines and treatments performed using them.

BRIEF DESCRIPTION OF THE FIGURES

Additional details and advantages in accordance with the teaching of the present invention will now be described in greater detail on the basis of the exemplary embodiments illustrated in the drawings, in which.

DETAILED DESCRIPTION OF THE FIGURES

Figure 1:
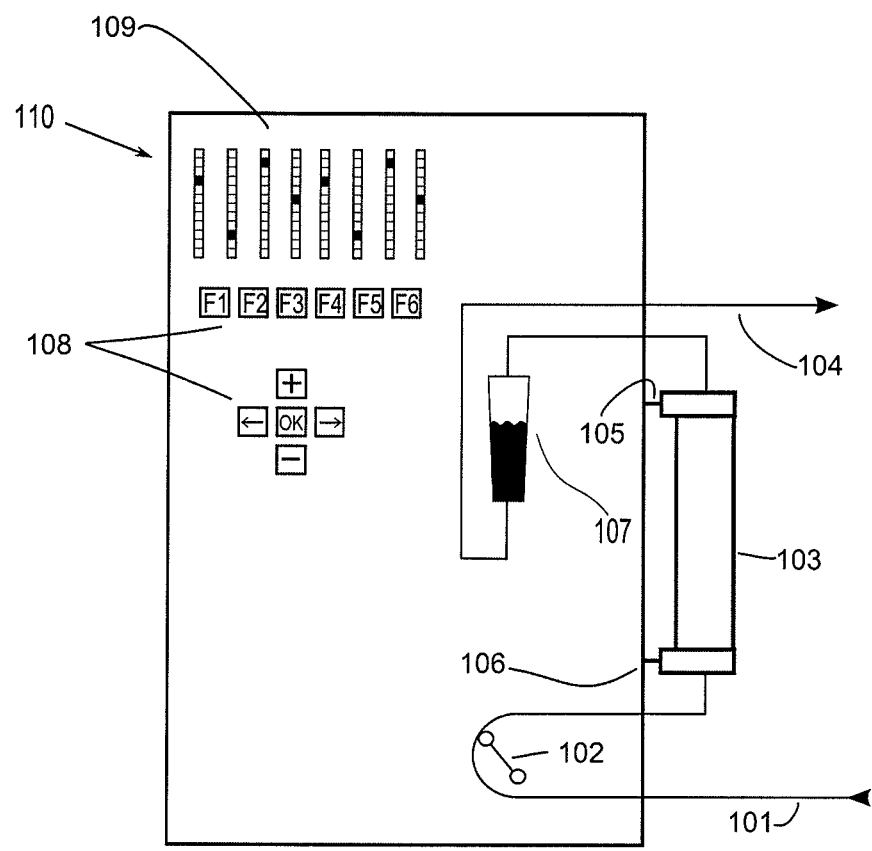
FIG. 1 shows a conventional medical fluid management machine, embodied as a hemodialysis machine, for example.

FIG. 1 shows a medical fluid management machine, which is embodied as a hemodialysis machine and is not equipped with its own display. Such dialysis machines were widely used mainly in the past and many of them are still in use today.

The dialysis machine 110 shows schematically parts of an extracorporeal blood circulation with an arterial blood line 101, which drains the blood from a patient (not shown). The blood pump 102 pumps the blood through a dialysis filter 103, which is equipped with a semipermeable membrane that separates the extracorporeal blood circulation semipermeably from a dialysate circulation. Treated blood is returned to the patient through the venous line 104 after any air bubbles that might be present in it have been expelled from the blood in the venous drip chamber 107. Dialysate is pumped by means of the dialysate lines 105 and 106 through dialysis filter 103, where it enters into a diffusive mass exchange with the patient's blood through the semipermeable membrane of the dialysis filter 103. If a pressure gradient is additionally built up from the blood side of the dialysis filter to the dialysate side of the patient, plasma water is expelled from the blood into the dialysate. Water can thus be withdrawn from the patient's blood. The dialysate is prepared in the hemodialysis machine 110 and is discarded after use. Devices may be provided on the hemodialysis machine, supplying a sterile substitution solution to the patient blood. This may take place upstream from the dialysis filter, in which case one speaks of predilution, or downstream from the dialysis filter, which is referred to as postdilution.

The filling level of blood in the venous drip chamber may optionally be monitored by various sensors in the dialysis machine.

The exemplary dialysis machine 110 is equipped with a number of LED strips 109 as the display device for important measured values such as blood pressure, ultrafiltration rate, substitution rate, blood flow rate, dialysate flow rate, etc. However, due to the limited number of LEDs in such an LED strip, its resolution is limited. Alternatively, and not shown in FIG. 1, for example, seven-segment LED displays may also be used.

Operator entries may also be input on the dialysis machine by using the operating keys 108.

In accordance with the present disclosure, such dialysis machines may be retrofitted with a connecting device for a mobile computer. In this way, a data interface to the mobile computer is also formed. Transmission of electric power from the dialysis machine to the mobile computer may advantageously also be set up.

Less convenient, older dialysis machines can be retrofitted inexpensively in this way to permit convenient operation.

As an alternative, dialysis machines having only small and/or inexpensive displays or none at all can be manufactured. Such dialysis machines are advantageous with respect to cost, manufacturing, maintenance and/or development. The user of dialysis machines often already has appropriate mobile computers, which may be used for various tasks on the dialysis machine.

Another advantage which is consistent with the teaching of the present invention is the possibility of being able to connect a single mobile computer to multiple different medical fluid management machines. For example, the treating physician or other medical personnel within a dialysis station may keep a single mobile computer on hand for dialysis machines that have only small and/or inexpensive displays or none at all and may connect this mobile computer to each dialysis machine in turn, respectively, with which they would like to interact. This makes it possible to further reduce costs within a dialysis station.

Figure 2:
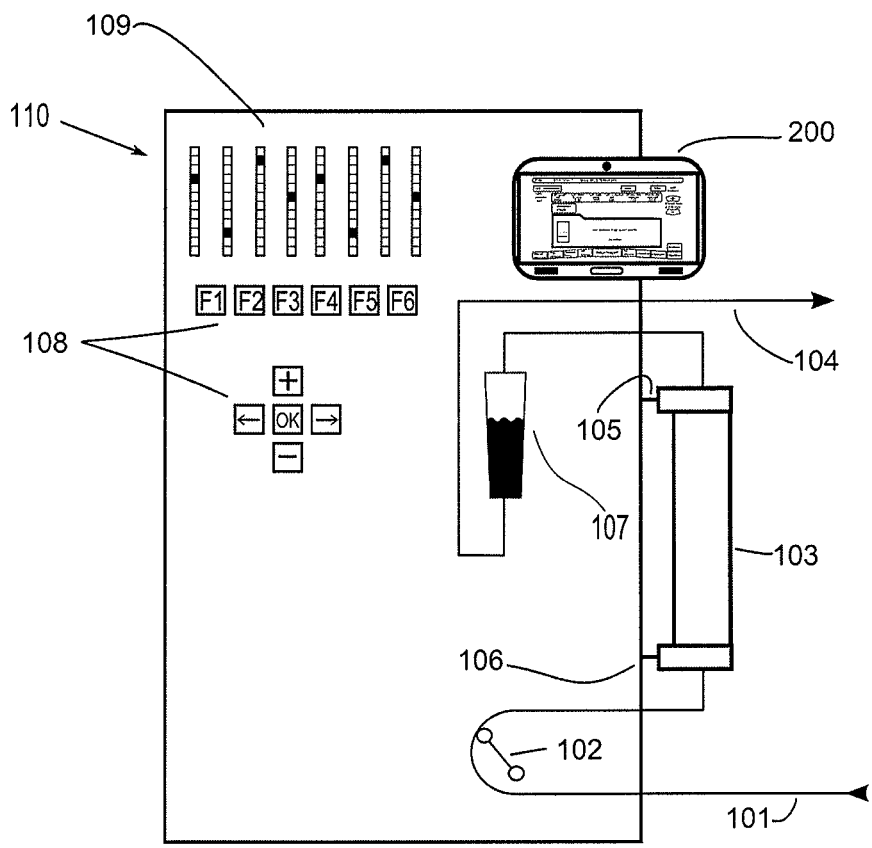
FIG. 2 shows a medical fluid management machine in accordance with the teaching of the present invention, embodied as a hemodialysis machine, for example, with a mobile computer embodied as a tablet PC, which serves as the display.

FIG. 2 shows a medical fluid management machine embodied as a hemodialysis machine, for example, having a mobile computer which is embodied as a tablet PC that serves as the display. In its dialysis-related functions, the dialysis machine corresponds essentially to the design of the hemodialysis machine, which is described in conjunction with FIG. 1 and to a description of which reference is herewith made instead of repeating the description. The same reference numerals correspond to the same or corresponding elements. In addition, a conventional tablet PC 200, which is connected to the dialysis machine 110 in a manner not shown in detail here, is also used. Various devices are suitable for connecting the tablet PC 200 to the hemodialysis machine 110. For example, a clamp may be attached to the hemodialysis machine for securely clamping the tablet PC. Such an approach has the advantage that no structural intervention in the tablet PC is necessary. The connecting device is advantageously designed so that various external devices such as smartphones or tablet PCs can be connected. This may be implemented, for example, by means of displaceable clamping mechanisms, which can be adapted to the dimensions of the external devices. The connection of the mobile computer may be accomplished in such a way that sensors already present on the mobile computer can record measured values pertaining to the dialysis machine or a treatment performed using the dialysis machine.

The connecting device may preferably be designed in such a way that the mobile computer is attached at a distance from the dialysis machine in order to permit a view of the extracorporeal blood circulation, for example, or parts of an extracorporeal blood circulation for a camera installed on the back of the external device.

Such a connecting device can be pulled out, rotated or pivoted, so that the mobile computer can be connected to the dialysis machine in any desired position.

Figure 3:
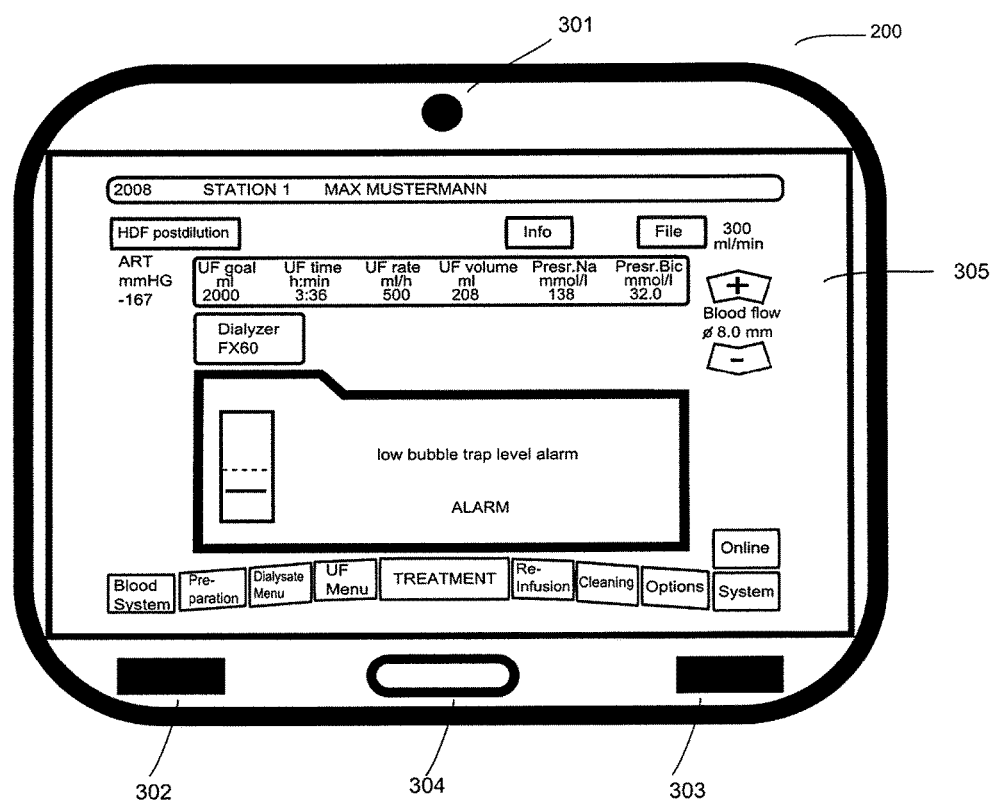
FIG. 3 shows a detailed view of the mobile computer from FIG. 2, embodied as a table PC.

FIG. 3 shows the mobile computer 200, which is embodied as a tablet PC and is described in conjunction with FIG. 2, shown here in a detail with typical display content.

In this example, the tablet PC 200 is equipped with a camera 301 on the front side of the display. Such tablet PCs are frequently also equipped with a camera device on the back side. In addition, the tablet PC 200 has two loudspeakers 302 and 303 and the microphone 304 as additional input and output devices. The display content 305 corresponds essentially to that for hemodialysis machines, which are equipped with an integrated display (often also embodied as a touchscreen). The information displayed here is significantly more extensive and more detailed than the information that can be displayed by a hemodialysis machine that does not have a display, such as that illustrated in FIG. 1. This includes, for example, the name of the machine (2008, station 1), the name of the patient (MAX MUSTERMANN), the type of treatment (HDF postdilution for hemodiafiltration with postdilution) and a variety of measured values and settings.

Furthermore, in the example in FIG. 3, an alarm message is also output on the display to draw attention to the fact that the blood level in the venous drip chamber is too low. The alarm-triggering state can be detected by the tablet PC itself, for example, in that a camera mounted on the rear of the tablet PC visually monitors the blood level in the venous drip chamber.

However, alarm status can also be transmitted from the dialysis machine to the table PC by data transmission. The alarm message may then be output in plain text on the display. This constitutes an advantage in comparison with an alarm display on a dialysis machine without its own display, which is often only symbolic and must be interpreted correctly by the operating personnel.

The present invention thus also contributes toward rapid and reliable detection of alarm states.

In addition, the operation of the dialysis machine may be simplified and made more convenient by using the touchscreen display, which is often provided on a mobile computer for this purpose. The input and output concept of modern dialysis machines having integrated touchscreen displays may be transferred to simpler older dialysis machines or to newly manufactured dialysis machines with simple and inexpensive equipment in this way, in that mobile computers are used as a complete substitute for a touchscreen display.

Figure 4:
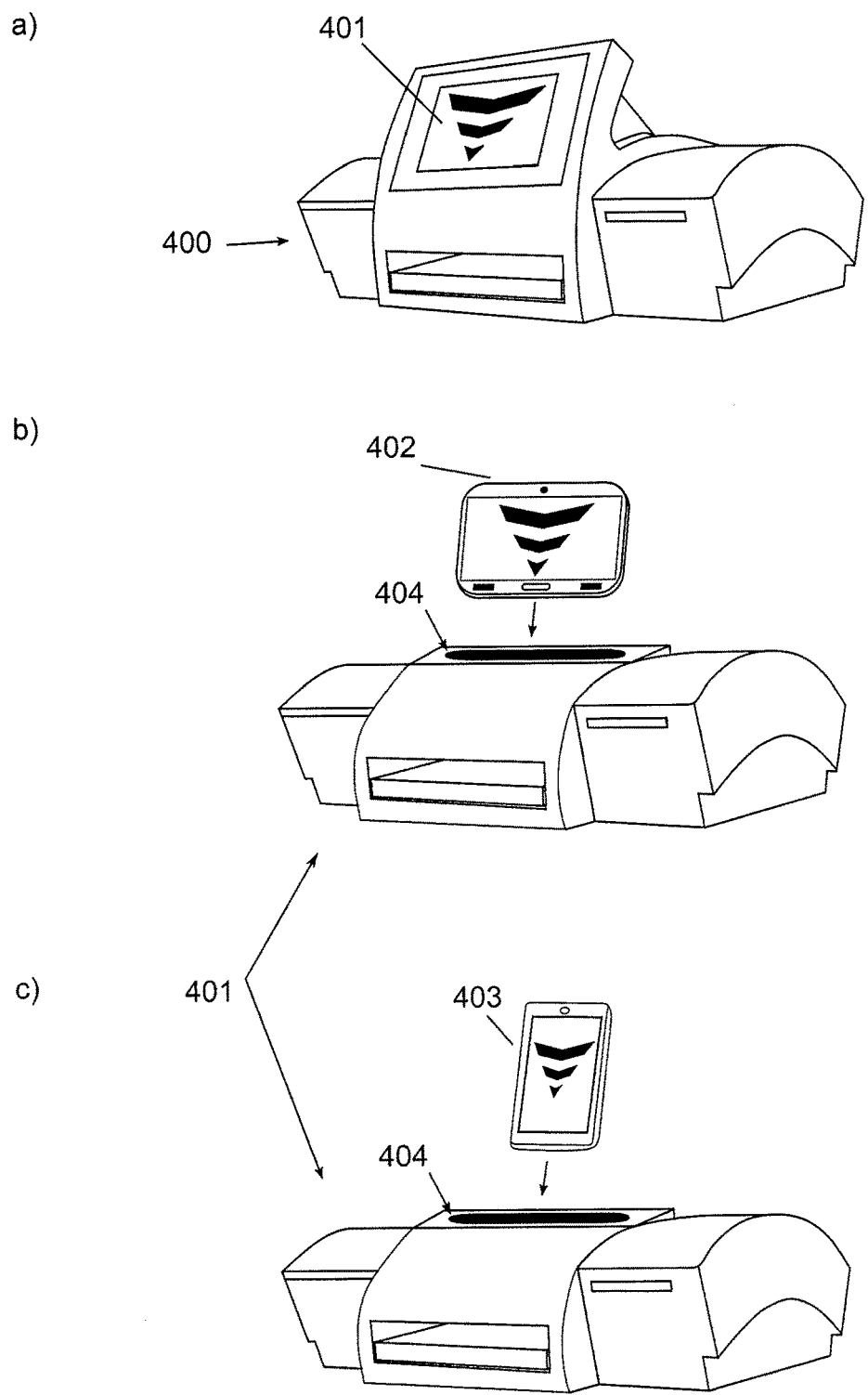
FIGS. 4a, 4b and 4c show a conventional medical fluid management machine, for example, as a peritoneal dialysis machine as well as in accordance with the teaching of the present invention with a smartphone and/or a PC tablet, each serving as a display for the peritoneal dialysis machine.

FIGS. 4b and 4c each shown embodiments of the invention for peritoneal dialysis machines. The peritoneal dialysis machine 400, which is shown in FIG. 4a, has a conventional design with an integrated display 401.

The two dialysis machines 401 in FIGS. 4b and 4c are equipped with a connecting device 404 and do not have their own display. The connecting devices in FIGS. 4b and 4c are embodied as a bay to receive a mobile computer as an example. It is conceivable that the bay also has electrical plug connectors, which can be connected to corresponding interfaces on the mobile computer.

FIG. 4b shows an embodiment with a tablet PC 402 as the mobile computer, and FIG. 4c shows an embodiment with a smartphone 403 as the mobile computer. In FIGS. 4b and 4c, the peritoneal dialysis machine is equipped with a connecting device 404, which is universally suitable for connecting multiple devices.

Any other connecting devices which may be embodied in the manner already described are also conceivable.

Figure 5:
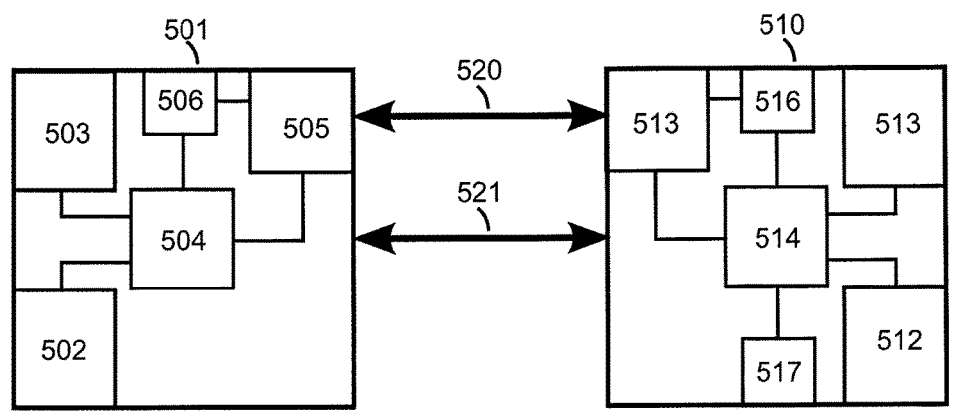
FIG. 5 shows a block diagram of a system of a medical fluid management machine and a mobile computer in accordance with the teaching of the present invention.

FIG. 5 shows schematically a medical fluid management machine 501 and a mobile computer 510 in accordance with the teaching of the present invention. The medical fluid management machine 501 has an input device 502 and advantageously also has an output device 503. The user can make operator entries by means of the input device 502. The input device may comprise keys, switches or keypads. The output device 503 outputs information pertaining to the medical fluid management machine and/or a treatment performed using the medical fluid management machine. The output device is advantageously embodied as a display. In accordance with the teaching of the present invention, a display may be omitted from the medical fluid management machine 501. In this case the output device 503 may be embodied in a simplified form, for example, using seven-segment LED displays or the like. However, in accordance with the teaching of the present invention, the output device 503 may also be omitted entirely. In one alternative embodiment, the input device 502 and the output device 503 are combined into one module, for example, as a touchscreen display. In addition, the medical fluid management machine 503 has a control unit 504, which comprises at least one CPU or a microcontroller. The control unit has an internal memory 506, into which computer programs for programming the control unit can be loaded by means of the data interface 505.

The mobile computer 510 illustrated schematically in FIG. 5 has a control unit 514, an internal memory 516, which can be loaded with computer programs for programming the control unit 514 by means of a data interface 513, and an input device 512 and an output device 513, which may also be combined in a combined input/output device. In the case of the exemplary embodiments, these input/output devices may advantageously be a touchscreen display on a smartphone or a tablet PC for the mobile computer 510. FIG. 5 also shows schematically a sensor 517 of the mobile computer 510. The sensor 517 may be used in a manner already described to detect sensor data pertaining to the medical fluid management machine 501 and/or a treatment performed using the medical fluid management machine 501. The sensor data may be processed by a data processing program in the control unit 514 or the sensor data may be relayed to the medical fluid management machine 501 by means of the data interface 513 and the data link 520. In any case, the sensor data may be used to monitor and/or control the medical fluid management machine 501 and/or a treatment performed using the medical fluid management machine 501.

The data link 520 establishes a connection, usually bidirectional, between the medical fluid management machine 501 and the mobile computer 510. The data link 520 may also be wireless in a form already described. Display information can be sent from the medical fluid management machine 501 to the mobile computer 510 over the data link, and input information and/or control signals can be sent from the mobile computer 510 to the medical fluid management machine 501 over the data link.

A mechanical connection of the mobile computer 510 to the medical fluid management machine 501 can be established by means of the connecting device 521 in a manner already described.

Figure 6:
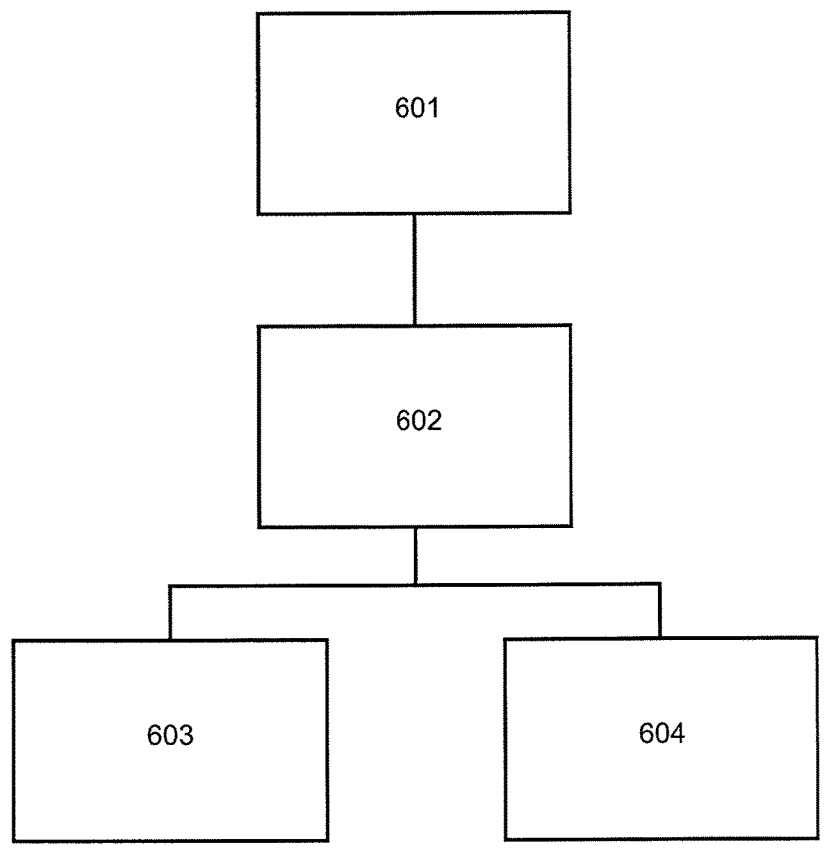
FIG. 6 shows a flow chart of a method in accordance with the teaching of the present invention.

FIG. 6 shows schematically a diagram of a method which is consistent with the teaching of the present invention. In step 601 the mechanical connection of the mobile computer 510 to the medical fluid management machine 501 takes place. Then in step 602 a data link is established between the medical fluid management machine 501 and the mobile computer 510.

The display of information pertaining to the medical fluid management machine 501 or a treatment performed using the medical management machine 501 is displayed in step 603 by means of the output device 513 of the mobile computer. Alternatively or in addition, the operation of the medical fluid management machine 501 by means of an input device of the mobile computer 510 takes place in step 604.

Figure 7:
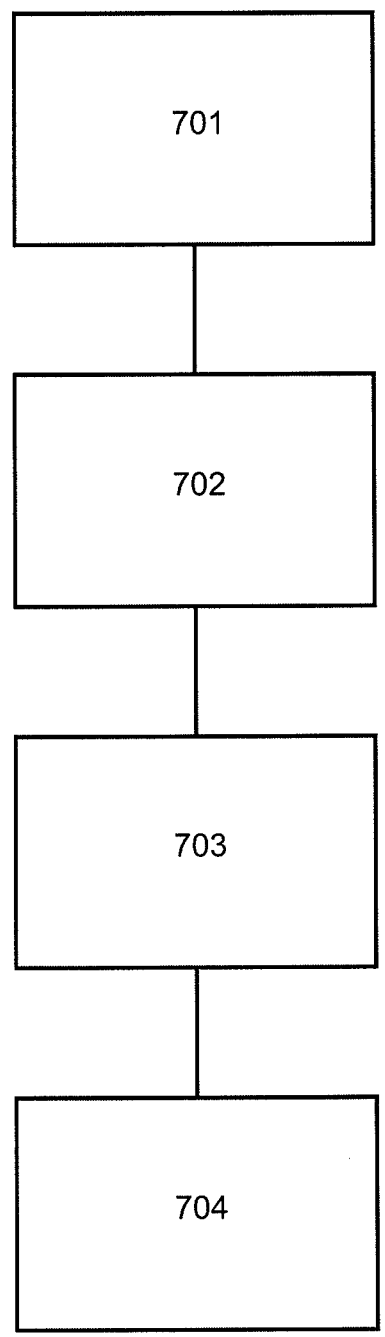
FIG. 7 shows a flow chart of another method in accordance with the teaching of the present invention.

FIG. 7 shows schematically a diagram of an additional method in accordance with the teaching of the present invention. The mechanical connection of the mobile computer 50 to the medical fluid management machine 501 takes place in step 701 in such a way that a sensor in the mobile computer 510 is able to record sensor values pertaining to the medical fluid management machine or treatment performed using the medical fluid management machine.

This may be accomplished in the manner already described in that the connecting device 521 is designed so that it can be rotated or pivoted or extracted, thus allow a sensor on the mobile computer, for example, a camera to be directed at the medical fluid management machine 501 or parts thereof, for example, to a venous drip chamber or to a patient being treated with the medical fluid management machine 501.

A data link is established between the medical fluid management machine 501 and mobile computer 510 in step 702.

Steps 701 and 702 may also be performed in the opposite chronological order.

The sensor values are recorded in step 703, and data processing of the sensor values is performed in step 704, and depending the results, the medical fluid management machine 501 is monitored and/or controlled or a treatment performed using the medical fluid management machine is monitored and/or controlled.

The data processing of the sensor values may be performed in the mobile computer 510 or in the medical fluid management machine 501 or in both. The data processing of the sensor values may include, for example: checking the filling level of a liquid in a container, checking the volume flow of a liquid in a container, checking the body temperature of a patient, checking the identity of the user of the mobile computer 510, recognizing a gesture by a patient or ascertaining the location of the mobile computer.

Depending on the outcome of the data processing, the medical fluid management machine 501 or a treatment performed using the medical fluid management machine 501 may be controlled and/or monitored in a manner as described above.

The disclosed teaching permits a variety of expansions of certain medical fluid management machines to include functions for which they had not previously been equipped, in that these functions are now taken over by mobile computers. Furthermore, the cost and effort for producing new medical fluid management machines can be greatly reduced by eliminating equipment using expensive input/output devices such as touchscreen displays. In contrast with medical fluid management machines, mobile computers are mass-produced items and therefore are inexpensive despite their versatility. The disclosed teaching makes use of this property and applies it advantageously to medical fluid management machines.

The invention claimed is:

1. A medical fluid management machine having an internal control unit, an operating unit connected to the internal control unit for operating the machine by operator entries, and an interface designed for data exchange with a mobile computer, wherein the machine is configured to cooperate with a mechanical connecting device designed for connection, positionally, to a suitably designed counterpart on the mobile computer, wherein the internal control unit is equipped to send information pertaining to the medical fluid management machine and/or a treatment performed using the medical fluid management machine by means of the interface to the mobile computer and/or to receive operator entries input on the mobile computer or to receive control signals from the mobile computer, and wherein the machine is configured to block operator entries from the operating unit to the internal control unit in response to the machine being linked for data exchange with the mobile computer.

2. A system comprising the medical fluid management machine according to claim 1 and a mobile computer having a computer control unit, an input and/or output device and an interface linked for data exchange with the medical fluid management machine interface, whereby the operating unit on the medical fluid management machine is blocked for operating the machine by operator entries, and configured for mechanically connecting to a mechanical connecting device designed for connection to a suitably designed counterpart on the medical fluid management machine, such that the computer control unit is equipped to display information on the output device, said information pertaining to the medical fluid management machine and/or a treatment performed using the medical fluid management machine and/or to relay operator entries that are input by means of the input device or to relay control signals to the medical fluid management machine by means of the interface.

3. The system according to claim 2, wherein the mobile computer further has at least one sensor which can detect at least one signal based on the medical fluid management machine and/or based on a treatment performed using the medical fluid management machine after the mobile computer has been connected to the medical fluid management machine, and wherein the control unit is equipped to relay control signals to the medical fluid management machine, said control signals depending on the detected signal and/or to output alarm messages which depend on the detected signal.

4. The system according to claim 3, wherein the sensor is a camera, a microphone, an inclination sensor, a vibration sensor, a touch-sensitive sensor, a fingerprint sensor, a UPS sensor or a temperature sensor, and wherein the control unit is equipped to determine with the detected signal the filling level of a liquid in a container, the volume flow of the liquid in a container, a patient's body temperature, the identity of the user, or to recognize gestures made by a patient, noises or accessory parts of the medical fluid management machine, to check the imperviousness of an extracorporeal blood circulation, to enable therapeutic options or to determine the location of the mobile computer.

5. The system according to claim 2, wherein the mobile computer interface is additionally configured to receive electricity from the medical fluid management machine.

6. The system according to claim 2, wherein the medical fluid management machine interface is configured for data exchange with at least one other device besides the medical fluid management machine.

7. The system according to claim 2, wherein the fluid management machine is a blood purification device.

8. The system according to claim 2 further comprising the mechanical connecting device mechanically connecting the mobile computer in a positionally maintaining manner to the medical fluid management machine.

9. The system according to claim 8, wherein the mechanical connecting device is selected from the group consisting of plug connectors, hooks, eyes, clamps, magnetic connections, and Velcro-type closures.

10. The system according to claim 8, wherein the mechanical connecting device provides rotatable positioning, pivotal positioning, pull-out positioning, or combinations thereof.

11. The machine according to claim 1, wherein the fluid management machine is a dialysis machine.

12. The machine according to claim 1, mechanically connected to the mechanical connecting device, which provides rotatable positioning, pivotal positioning, pull-out positioning, or combinations thereof.

13. A method for monitoring and/or controlling a medical fluid management machine or a treatment performed using the medical fluid management machine, wherein the medical fluid management machine has an internal control unit and an operating unit connected to the internal control unit for operating the machine by operator entries, comprising the steps of:

establishing a data link between the medical fluid management machine and a mobile computer equipped with an input for operating the medical fluid management machine, and an output for displaying information pertaining to the medical fluid management machine or a treatment performed using the medical fluid management machine, whereby the operating unit on the medical fluid management machine is blocked for operating the machine by operator entries from the operating unit in response to establishing the data link between the medical fluid management machine and the mobile computer, and at least one of displaying information pertaining to the medical fluid management machine or a treatment performed using the medical fluid management machine by means of the mobile computer output, or operating the medical fluid management machine by means of the mobile computer input.

14. The method of claim 13 further comprising the steps of:

mechanically connecting the mobile computer in a positionally maintaining manner to the medical fluid management machine in such a way that a sensor on the mobile computer is able to record sensor values pertaining to the medical fluid management machine or a treatment performed using the medical fluid management machine, recording the sensor values, data processing of the sensor values and, depending on the results, monitoring and/or controlling the medical fluid management machine or a treatment performed using the medical fluid management machine.

15. The method according to claim 14, wherein the sensor is a camera, a microphone, an inclination sensor, a vibration sensor, a touch-sensitive sensor, a fingerprint sensor, a GPS sensor or a temperature sensor.

16. The method according to claim 14, wherein the sensor signal is used to determine the filling level of a liquid in a container, the volume flow of a liquid in a container, a patient's body temperature, the identity of the user, to recognize a gesture made by the patient, noises or accessory parts on the medical fluid management machine, to check the imperviousness of an extracorporeal blood circulation, to enable therapeutic options or to determine the location of the mobile computer.

* * * * *